United States Patent [19]

Chen et al.

[11] Patent Number: 4,773,910
[45] Date of Patent: Sep. 27, 1988

[54] PERMANENT LIGAMENT PROSTHESIS

[75] Inventors: Elizabeth H. Chen; Alastair J. T. Clemow, both of Princeton, N.J.; Steven W. Arms, Burlington; Malcolm H. Pope, Shelburne, both of Vt.; Per Renstrom, Molyncke, Sweden

[73] Assignee: Johnson & Johnson Consumer Products, Inc., New Brunswick, N.J.

[21] Appl. No.: 85,823

[22] Filed: Aug. 17, 1987

[51] Int. Cl.⁴ ............................................. A61F 2/08
[52] U.S. Cl. ............................................. 623/13
[58] Field of Search .................. 128/1 R; 623/11, 1, 623/13, 16, 18

[56] References Cited

U.S. PATENT DOCUMENTS

| | | | |
|---|---|---|---|
| 3,896,500 | 7/1975 | Rambert et al. | 623/13 |
| 3,953,896 | 7/1976 | Treace | 623/13 |
| 4,209,859 | 7/1980 | Hoffman | 623/13 |
| 4,329,743 | 5/1982 | Alexander et al. | 623/13 |
| 4,483,023 | 11/1984 | Hoffman, Jr. et al. | 623/13 |

FOREIGN PATENT DOCUMENTS 2151487 7/1985 United Kingdom .

Primary Examiner—Richard J. Apley
Assistant Examiner—David J. Isabella
Attorney, Agent, or Firm—Michael Q. Tatlow

[57] ABSTRACT

A cruciate ligament prosthesis constructed with two separately tensionable strands. Each strand is composed of a plurality of fine polyolefin filaments, each filament having a diameter of from 25 to 50 microns and the breaking strength of each strand is at least 1000 pounds.

10 Claims, 3 Drawing Sheets

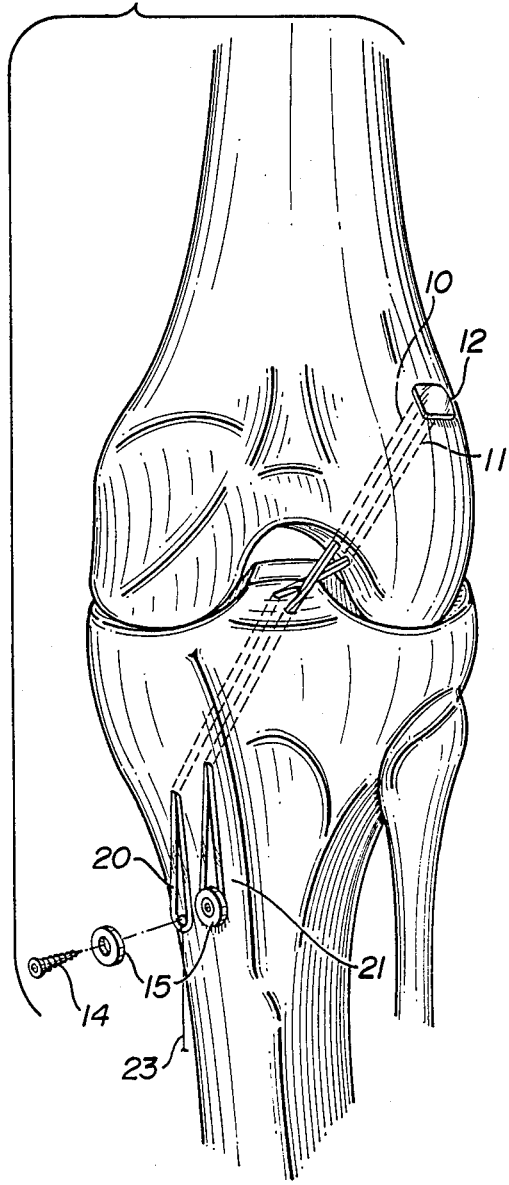
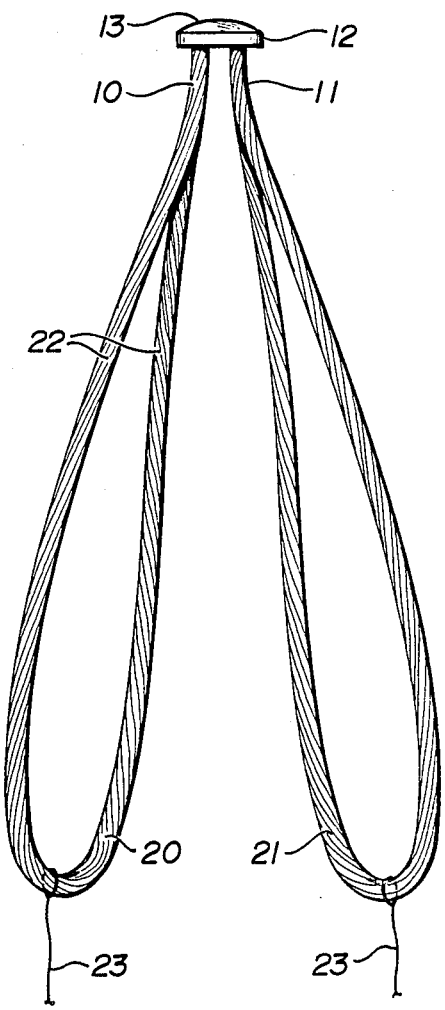
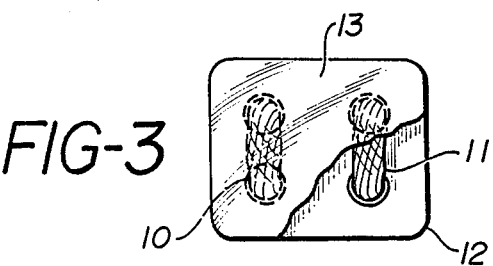

PERMANENT LIGAMENT PROSTHESIS

BACKGROUND OF THE INVENTION

The present invention relates to ligament prosthesis and more specifically to prosthetic devices to replace the cruciate ligament in a knee.

PRIOR ART

Various prosthetic devices have been developed to replace various ligaments in the human body. A number of these devices are indicated to be useful as a replacement for the cruciate ligament in a human knee. Examples of these devices are disclosed in the following patents:

U.S. Pat. No. 3,896,500 discloses a ligament prosthesis for replacing either one or both of the cruciate ligaments in a knee. Each ligament is composed of two strands of material wrapped in a single sheath.

U.S. Pat. No. 3,953,893 discloses a ligament prosthesis which is made from an ultrahigh molecular weight polyethylene rod-shaped bridge member which has a particular attachment mechanisms to attach the bridge member prostheses in the bone.

U.S. Pat. No. 4,329,743 discloses a ligament prosthesis made from carbon fibers coated with an absorbable polymer. The carbon fibers have a tendency to mechanically degrade with time and release carbon particles into the implantation site.

U.S. Pat. Nos. 4,483,023 and 4,209,859 disclose a ligament prosthesis which is made from high strength polyethelyne terathalate. This device is used as an augmentation device to a natural tissue graft. It has high strength but because of its construction. it has a tendency to stretch out when it is used which causes a loss in functionality.

EPO Pat. No. 0106,501 discloses a loosely braided oriented polytetrafluoroethylene ligament prosthesis. The fibers are made with expanded polytetrafluoroethylene and allow ingrowth of both tissue and bone. This device has a tendency to fray at its edges where it passes through bone and has been recommended for use only in limited applications.

British Pat. No. 2,151,487A discloses a ligament prosthesis comprising a core of carbon fiber and a braided sheath over the core.

Generally, the devices mentioned above also do not anatomically reproduce the structure or function of the human cruciate ligament.

SUMMARY OF THE PRESENT INVENTION

The present invention is directed towards a cruciate ligament prothesis which can be employed as a replacement for either the anterior or posterior cruciate ligament in a human knee. The present ligament prothesis is better able to anatomically reproduce the function and properties of natural cruciate ligaments. The present ligament prosthesis is made with two separate small diameter strands of fibrous material each of which are capable of being independently tensioned to thereby provide support for the knee through a wider range of flexion than has been provided by prior art devices. The separate strands of the present prosthesis can more accurately reproduce the function of the anteromedial and posterolateral bands of the anterior cruciate ligament than a prosthesis made from a single strand of material.

BRIEF DESCRIPTION OF THE DRAWINGS

FIG. 1 is an isometric view showing the positioning of the ligament of the present invention in a human knee.

FIG. 2 is a plane view of the ligament of the present invention.

FIG. 3 is a particularly fragmented view of a portion of the ligament prosthesis of the present invention.

DETAILED DESCRIPTION OF THE INVENTION

Figure 6:
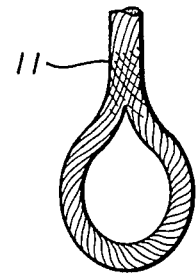
FIG. 6 shows a second embodiment of an end of the prosthesis of the present invention.

The prosthetic ligament of the present invention is composed of two independent strands of fibrous materials 10 and 11 (FIG. 2 ) Each of these strands is made from a very high tenacity biocompatible fibrous material. Each of the strands is anchored in a button 12 at one end and has a loop 20 or 21 at the other end. The loop may be formed by anchoring both ends of a strand in the button 12 as shown in FIG. 3. Each of the individual strands 10 or 11 can be made from two individual tows 22. The tows can be twisted together to form a single strand with a loop end as shown in FIG. 6 or the tows may be formed into large loops as shown in FIG. 2. The tows are formed by combining a number of individual yarns as furnished by the manufacturer. The number of individual yarns employed to form the tow can be varied depending on tbe ultimate strength that is desired in the prosthesis. The yarns in turn are made of a number of small individual filaments each filament having a diameter of from about 25 to 50 microns and preferably between 30 and 40 microns. The number of filaments in each strand can be varied as desirable to give the individual strands different strength characteristics. Generally there are between 8000 and 14,000 individual filaments in each strand. The fiber materials that have been found to be useful in the ligament of the present invention are polyolefins such as high molecular weight polyethelyne and ultrahigh molecular weight polypropylene. These materials are much more flexible and abrasion resistant than the prior art carbon fibers and do not break into hard fragments or particles when implanted. The preferred material is a high tenacity polyethylene fiber available from Allied Corporation and sold under the designation SPECTRA 900 or SPECTRA 1000. The individual filaments have a diameter of approximately 38 microns and a number of individual filaments are present in the yarn which makes up the strand. It should be understood that these filaments are not round but are somewhat rectangular. The nominal diameter of the filaments are the values given above. In a typical construction approximately 118 filaments are present in each yarn. The tenacity of the yarns of this material is approximately 30 to 40 grams per denier or a tensile strength of 375,000 psi. A sufficient number of yarns are combined in each strand to give the desired breaking strength to the strand. A breaking strength of at least 1000 pounds for each strand is the minimum desired breaking strength. This tensile strength or breaking strength is more than adeguate to provide the strength necessary in a ccuciate ligament prosthesis.

The high tenacity of the filaments allows the prosthesis to be constructed with a minimum diameter and therefor the prosthesis can be implanted with minimum bone removal. The diameter of each strand is between 2 and 6 millimeters. preferably between 4 and 6 millimeters. The diameter of the strands is relatively uniform throughout its length. In addition. these high tenacity polyethylene yarns have excellent abrasion resistance.

The prosthesis of FIGS. 2 and 3 is fabricated by taking a tow containing a requisite number of individual filaments and passing the tow through the button 12 shown in FIGS. 2 and 3. The length on the resulting strand. that is the length of each loop, is between 8 and about 13 centimeters for normal adult knee prostheses. It should be understood that the length of the prosthesis would be varied when used in animals or in smaller humans. The tows are knotted on the top surface of the button and then the knotted tows are held in place by coating the top of the button with a potting compound 13 such as a biocompatible adhesive material. A suitable potting compound for use as the adhesive material is a medical grade of epoxy resin.

The yarns making up the strand have very little twist, i.e., a twist of less than 3 twist per inch and preferably is 0 twist per inch.

The low twist of the strand leaves a maximum opening between the filaments to allow bone ingrowth into the space between the filaments. The low twist provides maximum immediate strength when the strands are stressed. If the strands were braided or highly twisted the application of force would tend to first eliminate the twist or stretch a braid when the force is first applied, which tends to stretch the prosthesis and adversely changes the tension of the strands.

At the bottom of eaoh loop there is a guide thread 23 attached to the loop. This thread may be a surgical grade metal. i.e., stainless steel, suture material and is used to thread the ligament prosthesis loops through the knee upon implantation.

The button 12 is rectangular or square approximately 10 to 15 millimeters on each side and approximately 3 millimeters thick. The button is made of medical grade stainless steel, titanium or other biocompatible material. As shown in FIG. 3, there are four holes in each button. The holes are drilled through in the button in pairs to accommodate the insertion and locking of the strands. Each of the holes is approximately 4 to 6 millimeters in diameter and the holes holding the ends of either loop are approximately 4 to 6 millimeters apart. The pairs of holes are placed approximately 5 to 8 millimeters apart in the button. The use of the button 12 eliminates the need to drill additional holes in the bone to anchor the proximal end of the prosthesis. The looped ends of the prosthesis are held in position by screws 14 and washers 15.

Figure 4:
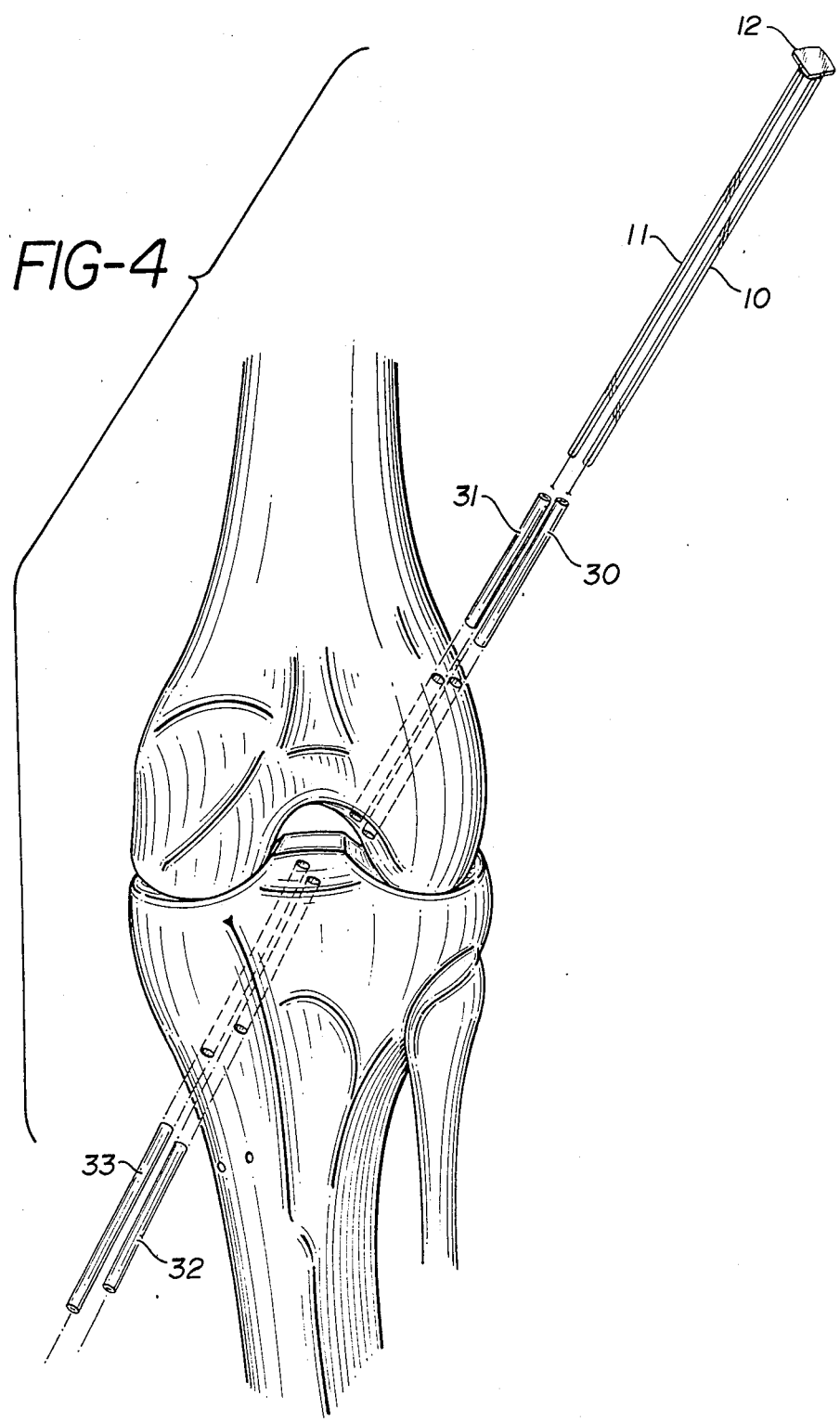
FIG. 4 is an isometric view of a portion of another embodiment of the invention and its positioning in a human knee.
Figure 5:
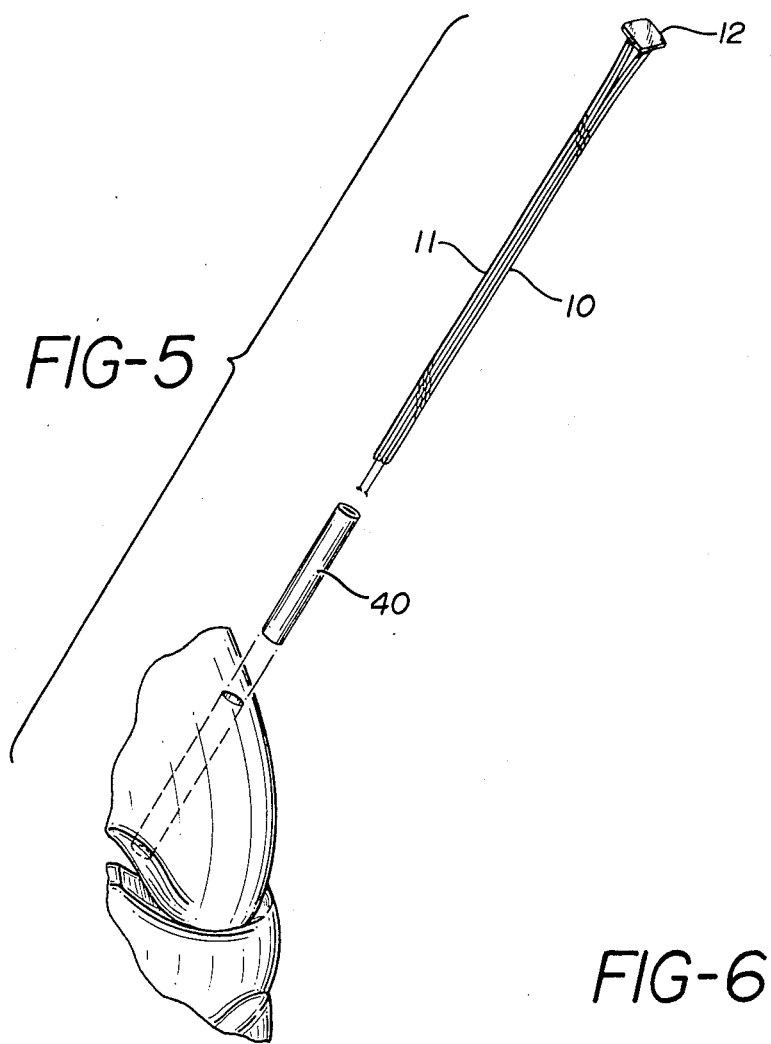
FIG. 5 shows another embodiment of the present invention.

All or a portion of the strands at either or both ends of the prosthesis that are in direct contact with bone may be encased or embedded in a hard plastic sleeve as illustrated in FIGS. 4 and 5. The purpose of the plastic sleeve is to prevent excessive localized force being applied to the bone tunnel which might cause the location of the strands to move or drift in the bone. Bone has a tendency to resorb away from a prosthesis which is exerting excessive force against the bone. The plastic sleeves 30 and 31 in FIG. 4 are illustrated as hollow tubes through which the strands 10 and 11 are threaded. FIG. 4 shows separate sleeves 30 and 31 for the strands 10 and 11 passing through the femoral portion of the knee and separate tubes 32 and 33 for the strands passing through the tibial portion of the knee. FIG. 5 shows a single sleeve 40 for the strands passing through the femoral portion of the knee. Rather than use a separate sleeve in a tubular form as illustrated in the drawings, it is also possible to embed the portion of the strands that will be in contact with the bone in a potting material. However. it must be understood that the separate strands 10 and 11 must be capable of being individually tensioned. Therefore, it is not possible to embed the strands together in both the femoral end and the tibial end of the prosthesis. If the strands at both ends of the prosthesis are embedded together it will not be possible to individually adjust the tension of the strands.

The materials used as the sleeves or the potting compounds must be a biocompatable material such as polyethylene, polysulfone, polymethylmethacrylate or polyurethane. The materials may be formed so that they are porous to encourage bony ingrowth into the sleeve to assist in the fixation of the prosthesis.

It is also possible to cover the strands with a braided or knitted tubular fabric so long as the strands are movable within the tubular fabric so that each strand may be separately tensioned.

The prosthesis for the anterior cruciate ligament is implanted by the following procedure. An incision is made to reveal both the femoral and tibial portion of the knee. Two holes are drilled through the femoral portion into the interior of the knees joint at the point of attachment of the natural ligament. Two additional holes are drilled from the areas below the tibial plateau of the knee into the interior of the knee joint emerging at the point of attachment of the natural ligament. The guide thread is passed through the drilled holes and the individual loop threads are passed through the femoral portion of the knee into the joint and through the tibia to exit below the tibia plateau. The guide threads can then be removed from the prosthesis. The individual loops can be separately tensioned to provide the optimum support throughout different ranges of flexion of the knee. For example, one of the strands could be tensioned so that it is tight in extension and loose in flexion and the other strand could be tensioned to be loose in extension and tight in flexion. This capability more closely mimics the function of the anteromedial and posterolateral bands of a natural anterior cruciate ligament. Each loop is placed by adjusting the tension to the desired level at the particular degree of flexion selected by the surgeon. A hole is drilled into the bone at the proper location to fix the loops. The screw 14 is threaded through the washer 15 and a loop placed between the washer and the bone. The screw is then secured to the bone to affix the particular loop in its proper position to give the desired tension.

Because each individual strand can be adjusted to the proper tension over a different range of flexion, the prosthesis of the present invention more anatomically mimics the mechanics of the human cruciate ligament through different ranges of flexion.

The prosthesis is shown in the drawings with the button 12 at the femoral end of the prosthesis so that the strands are individually tensioned at the tibial end of the prosthesis. The prosthesis may be implanted in the reverse sequence, i.e., the button 12 at the tibial end of the prosthesis and the strands may be tensioned at the femoral end of the prosthesis.

We claim:

1. An anterior cruciate ligament prosthesis comprising two strands, each of said strands having a proximal and a distal ends and being formed of a plurality of individual fine filaments of high tenacity polyolefin fibers, said strand having a breaking strength of at least 1,000 pounds and a cross-sectional diameter of between 2 and 6 millimeters; the proximal ends of each of said strands being affixed to a single button means and each strand forming a loop at said distal end; and a removable guide thread attached to said loop, said removable guide thread having a predetermined length to thread each strand from a joint from a proximal point of attachment to a distal point of attachment.

2. The prosthesis of claim 1 in which said button has a top surface and a bottom surface, a knotted end of each strand in on the top surface of said button and is embedded in an adhesive overlying the top surface of the button.

3. The prosthesis of claim 1 in which the fibers of said strands are polyethylene.

4. The prosthesis of claim 1 in which each strand contains from 8,000 to 14,000 filaments.

5. The prosthesis of claim 4 in which the diameter of each filament is between 30 and 40 microns.

6. The prosthesis of claim 2 in which each strand is a continuous length of yarn, and the ends of said yarn are knotted on the top surface of said button.

7. The prosthesis of claim 2 in which each loop is threaded through two holes in said button.

8. The prosthesis of claim 1 in which at least a portion of the strands are encased in a biocompatible plastic material.

9. The prosthesis of claim 1 in which the strands have a diameter between 4 and 6 millimeters.

10. The prosthesis of claim 1 in which the strands have a twist of less than three twists per inch.

* * * * *